United States Patent
Kitamura et al.

(10) Patent No.: US 6,972,347 B1
(45) Date of Patent: Dec. 6, 2005

(54) METHOD FOR CONVERTING AROMATIC HYDROCARBONS

(75) Inventors: Akira Kitamura, Nagoya (JP); Ryoji Ichioka, Nagoya (JP); Shinobu Yamakawa, Nagoya (JP)

(73) Assignee: Toray Industries, Inc., (JP)

( * ) Notice: Subject to any disclaimer, the term of this patent is extended or adjusted under 35 U.S.C. 154(b) by 0 days.

(21) Appl. No.: 09/589,588

(22) Filed: Jun. 8, 2000

(30) Foreign Application Priority Data

Jun. 16, 1999 (JP) ............................. H11-169100

(51) Int. Cl.⁷ ................................ C07C 5/00

(52) U.S. Cl. ...................................... 585/475; 585/470

(58) Field of Search ............................. 585/470, 475, 585/448, 488, 489

(56) References Cited

U.S. PATENT DOCUMENTS

| 3,632,835 A | | 1/1972 | Mitche et al. ............... 260/666 |
| 4,016,218 A | * | 4/1977 | Haag et al. ................. 585/467 |
| 5,030,786 A | * | 7/1991 | Shamshoum et al. ....... 585/467 |
| 5,952,535 A | * | 9/1999 | King et al. ................. 585/475 |

FOREIGN PATENT DOCUMENTS

| GB | 1 542 774 | 3/1979 |
| WO | WO 96 24568 | 8/1996 |
| WO | WO 98 12159 | 3/1998 |

* cited by examiner

Primary Examiner—Thuan D Dang
(74) Attorney, Agent, or Firm—DLA Piper Rudnick Gray Cary US LLP

(57) ABSTRACT

A method for converting aromatic hydrocarbons by contacting an aromatic hydrocarbon starting material including benzene and having a non-aromatic compound content of 1% by weight or less, with a catalystto generate useful C7 and C8 aromatic hydrocarbons while reducing the catalyst deactivation.

5 Claims, No Drawings

METHOD FOR CONVERTING AROMATIC HYDROCARBONS

BACKGROUND OF THE INVENTION

1. Field of the Invention

The present invention relates to a method for converting aromatic hydrocarbons, more precisely to a method for converting a starting aromatic hydrocarbon material containing benzene with efficiently increasing useful aromatic hydrocarbons such as C7 and C8 aromatic hydrocarbons and with reducing catalyst deactivation. (The wording "C7–, C8 and C9+hydrocarbons" referred to herein is meant to indicate hydrocarbons having at most 7 carbon atoms, those having 8 carbon atoms and those having at least 9 carbon atoms, respectively, and the same shall apply hereinunder unless otherwise specifically indicated.)

2. Description of the Related Art

Requirements for regulating environmental problems are being much severer these days. Above all, there is much increasing a demand for cleaner fuel. Regarding gasoline, in particular, the influence of benzene therein on human health is being a serious problem. In the United States, the benzene content of gasoline is regulated. Also in Japan and Europe, it is being regulated, and oil companies are tackling the problem of reducing the benzene content of gasoline.

To meet the market needs of high-octane fuel, benzene and alkyl-aromatic hydrocarbons such as toluene and xylene having a high octane value have heretofore been much in gasoline as important gasoline bases, and their concentration in gasoline is high. In general, gasoline is produced in an oil refining process including catalytic reforming and cracking steps, in which the distillates fractionated in each step contain benzene. In the case where benzene is removed from gasoline so as to meet the environmental requirements mentioned above, a relatively large amount of benzene shall be extracted out of gasoline, and effective use of benzene is an emergent problem in the art. For utilizing it, known is a technique of mixing benzene with C9+ aromatic hydrocarbons to yield toluene and xylene through transalkylation. At present, it is said that toluene and xylene have no problematic influence on human health, unlike benzene. In addition, since toluene and xylene have a higher octane value than benzene, the transalkylation to produce them is preferred for increasing the octane value of gasoline.

In general, benzene having been extracted out of gasoline is separated from gasoline through distillation. The benzene fraction contains a large amount of non-aromatic compounds of which the boiling point range is near that of benzene, especially non-aromatic hydrocarbons such as olefins and naphthenes. In the case where the benzene fraction containing such a large amount of non-aromatic compounds is directly transalkylated with C9+ aromatic hydrocarbons in the presence of hydrogen, the aromatic transalkylation is often accompanied by a side reaction of paraffin decomposition. The side reaction of paraffin decomposition is troublesome in that its hydrogen consumption is large and the reaction system is undesirably heated owing to the decomposition heat.

U.S. Pat. No. 5,347,061 discloses a method of converting benzene in a gasoline distillate, and C9+ hydrocarbons, into C7 and C8 alkyl-aromatic hydrocarbons. In this, a benzene-rich C6 hydrocarbon stream derived from distillation of reformed gasoline, and a C9+ hydrocarbon stream are converted into C7 and C8 aromatic hydrocarbons through cracking, transalkylation and alkylation in the presence of an acidic metallosilicate catalyst. However, in the U.S. Pat. No. 5,347,061 method, the C9+ hydrocarbon is positively subjected to catalytic cracking to produce an alkylating agent for benzene alkylation, for which, therefore, the production of a non-aromatic hydrocarbon is indispensable.

Japanese Patent Laid-Open No. 38497/1997 discloses a method for converting aromatic hydrocarbons, in which a starting material that comprises a benzene-containing distillate from a catalytically-reformed product of naphtha, and a trialkylbenzene-containing distillate from a catalytically-cracked product, is transalkylated in the presence of a crystalline aluminosilicate catalyst that carries a metal component of Group VIII of the Periodic Table therewith, to give a reaction product essentially comprising monoalkylbenzenes and dialkylbenzenes. It is stated that mordenite having a low morphology selectivity index is poorly practicable for the conversion as deactivating much through coking, while TSZ is preferred as its total adsorption capacity and morphology selectivity index are both large. The term "total adsorption capacity" referred to therein is meant to indicate the total of toluene, 1,2,4-trimethylbenzene and 1,2,3-trimethylbenzene adsorbed by the catalyst (in terms of ml/100 g of the catalyst, crystalline aluminosilicate); and the term "morphology selectivity index" is meant to indicate the ratio of toluene adsorption capacity/(1,2,4-trimethylbenzene+1,2,3-trimethylbenzene) adsorption capacity of the catalyst.

Japanese Patent Laid-Open No. 155198/1997 discloses a method for converting C9+ aromatic hydrocarbon compounds in crude oil having a specific boiling point range and not containing benzene, into toluene and C8 aromatic hydrocarbon compounds, in the presence of hydrogen and by the use of a catalyst of a metal selected from metals of Group VIII and Group VIA of the Periodic Table or its compound carried by a carrier that contains zeolite having a maximum micropore diameter of from 0.6 to 1.0 nm and having a ratio of $SiO_2/Al_2O_3$ of at least 50. In this, it is indicated that mordenite is preferred as the specific zeolite to be used, and nickel, palladium and molybdenum are preferred as the metal.

Japanese Patent Laid-Open No. 38505/1997 discloses a method for converting benzene and C9+ aromatic hydrocarbon compounds in crude oil having a specific boiling point range, into toluene and C8 aromatic hydrocarbon compounds, in the presence of hydrogen and by the use of a catalyst of a metal selected from metals of Group VIII and Group VIA of the Periodic Table or its compound carried by a carrier that contains zeolite having a maximum micropore diameter of from 0.6 to 1.0 nm and having a ratio of $SiO_2/Al_2O_3$ of at least 50.

Japanese Patent Laid-Open No. 187658/1997 discloses a method for converting benzene and C9+ aromatic hydrocarbon compounds in crude oil having a specific boiling point range, into toluene and C8 aromatic hydrocarbon compounds, in the presence of hydrogen and by the use of a catalyst of a metal selected from metals of Group VIII and Group VIA of the Periodic Table or its compound carried by a carrier that contains zeolite having a maximum micropore diameter of from 0.6 to 1.0 nm and having a ratio of $SiO_2/A_2O_3$ of smaller than 50.

PCT application No. 98/12159 discloses a process for converting an aromatic material that contains ethyl or propyl-containing C9 hydrocarbon compounds in an amount of at least 20%, into a toluene and xylene-rich product, in which the starting aromatic material is contacted with a catalyst that contains palladium-carrying de-aluminated mordenite having a silica/alumina ratio of from 12 to 30, in the presence of hydrogen to produce the product.

PCT application No. 96/24568 discloses a process for converting a material that contains C9+ aromatic hydrocarbons, and benzene and/or toluene, into C9– (excluding C9) aromatic hydrocarbons, in which the starting material is contacted with a catalyst that contains zeolite having a control index of from 0.5 to 3 and in which the catalyst has a hydrogenation site but has been so processed that its nucleus hydrogenation capacity is reduced.

U.S. Pat. No. 5,406,016 discloses a process for converting benzene and a C10+ alkyl-aromatic compound having at least 2 alkyl groups, into methylbenzenes, in which the starting compounds are processed with a 12-membered cyclic zeolite under a specific reaction condition.

In these examples, however, the aromatic compound conversion efficiency is low, and the references noted above say nothing how to treat non-aromatic compounds that may be present in the starting materials.

SUMMARY OF THE INVENTION

One object of the present invention is to convert a benzene-containing, aromatic hydrocarbon material into C7, C8 and other useful aromatic hydrocarbons in the presence of a catalyst, increasing the content of the useful aromatic hydrocarbons in the converted product.

Another object of the invention is to convert a benzene-containing, aromatic hydrocarbon material into such useful aromatic hydrocarbons in the presence of a catalyst, while reducing the benzene content of the converted product.

Still another object of the invention is to convert a benzene-containing, aromatic hydrocarbon material into such useful aromatic hydrocarbons in the presence of a catalyst, while reducing catalyst deactivation.

Still another object of the invention is to convert a benzene-containing, aromatic hydrocarbon material into such useful aromatic hydrocarbons in the presence of a catalyst and hydrogen, while reducing hydrogen consumption.

To attain the objects as above, the invention provides a method for converting aromatic hydrocarbons, which comprises contacting a starting material of aromatic hydrocarbons that contains benzene and has a non-aromatic compound content of at most 1% by weight, with a catalyst; and provides a method for converting aromatic hydrocarbons, which comprises removing non-aromatic compounds from a starting material of aromatic hydrocarbons that contains benzene and non-aromatic compounds so as to reduce the non-aromatic compound content of the starting material to 1% by weight or less, followed by contacting the material with a catalyst.

DESCRIPTION OF THE PREFERRED EMBODIMENTS

The invention is described in detail hereinunder.

In the invention, a benzene-containing, aromatic hydrocarbon material which has a non-aromatic compound content of at most 1% by weight is converted.

Preferably, the starting material is prepared from a crude material having a non-aromatic compound content of at least 1% by weight, by removing non-aromatic compounds therefrom to reduce the non-aromatic compound content of the material to at most 1% by weight. The converted aromatic hydrocarbons may be used as starting materials for ordinary chemicals. In the case where a benzene distillate from gasoline is used as the starting material in the invention, the converted aromatic hydrocarbons may be used as additional gasoline bases for the benzene-poor gasoline. In that manner of one preferred embodiment, the invention is favorable for effectively utilizing benzene extracted from gasoline.

Non-aromatic compounds referred to herein are compounds except aromatic hydrocarbons, concretely including non-aromatic hydrocarbons such as paraffins, olefins, naphthenes, etc. The invention is characterized in that the starting material of benzene-containing aromatic hydrocarbons has a non-aromatic compound content of at most 1% by weight.

"Aromatic hydrocarbon conversion" in the invention concretely indicates a reaction selected from the group consisting of at least one of transalkylation, dealkylation and disproportionation. The reaction is effected under conditions under which at least one transalkylation, dealkylation and disproportionation reaction is effected, generally in the presence of hydrogen. The reaction pressure may fall between 0.1 and 100 MPa, preferably between 0.5 and 60 MPa, more preferably between 1 and 50 MPa. If the reaction pressure is too low, the catalyst used will soon deactivate and the reaction speed will lower; but if too high, it is uneconomic for the cost of equipment. The reaction temperature may fall between 200 and 650° C., preferably between 250 and 500° C. If the reaction temperature is too low, the reaction speed will lower; but if too high, the aromatic hydrocarbons being processed will much decompose and the catalyst used will soon deactivate. The hydrogen flow rate may fall between 0.1 and 20, preferably between 0.5 and 10 in terms of hydrogen/starting material (mol/mol). If the hydrogen flow rate is too low, the catalyst used will soon deactivate; but if too high, it is uneconomic.

The starting material to be processed in the invention contains aromatic-hydrocarbons with benzene. The aromatic hydrocarbons include benzene, toluene, xylene, ethylbenzene, trimethylbenzene, ethyltoluene, propylbenzene, tetramethylbenzene, ethylxylene, diethylxylene, propyltoluene, and other aromatic hydrocarbons. In case where the starting material is converted into a product containing toluene and/or xylene, the toluene and/or xylene content of the starting material shall be lower than the equilibrium composition of toluene and/or xylene in the starting material.

The starting material may be any ones to be obtained in ordinary oil refineries and having a boiling point that falls within a gasoline boiling point range, including, for example, catalytically-reformed oil, etc. If desired, oil fractions obtained in oil refineries may be combined for the starting material. In general, refined oil, especially catalytically-reformed oil can be fractionated into C5–, C6, C7, C8, C9+ and other fractions through distillation, depending on their boiling point ranges. After having been thus fractionated, different fractions may be combined for the starting material to be processed in the invention. As the case may be, refined oil may be directly the starting material for the invention, without being fractionated into different fractions. Anyhow, the starting material to be processed in the invention must contain benzene.

In general, reformed oil fractions having fewer carbon atoms have a higher non-aromatic compound content. For example, the non-aromatic compound content of the C6 fraction of reformed oil may be higher than 50%. Preferably, the non-aromatic compounds in the oil fractions are removed from the aromatic compounds therein through distillation or extraction. The starting material or aromatic compounds, from which non-aromatic compounds have been removed and which therefore has a non-aromatic compound content of at most 1% by weight, is converted by contacting it with a catalyst in the invention.

The starting material of benzene-containing aromatic compounds to be processed in the invention is characterized in that its non-aromatic compound content is at most 1% by weight. If the non-aromatic compound content of the starting material is larger than 1% by weight, the conversion of the starting material into C7, C8 and other useful aromatic hydrocarbons is poor. If so, in addition, the starting material will much decompose and will therefore generate much decomposition heat, while consuming much hydrogen, with the result that the decomposed products will seriously deactivate the catalyst used. Preferably, the non-aromatic compound content of the starting material is at most 0.5% by weight, more preferably at most 0.1% by weight.

Preferably, the crude starting material is distilled or extracted to remove non-aromatic compounds from it. Removing non-aromatic compounds from the starting material may be effected either before or after the starting material is fractionated into different fractions through distillation, but indispensably before it is subjected to the reaction for conversion. The non-aromatic compounds thus separated from the starting material may be used as gasoline bases either directly or after having been isomerized to increase their octane value.

The benzene content of the aromatic hydrocarbon material to be processed in the invention is not specifically defined, but may fall generally between 5 and 80% by weight, preferably between 10 and 70% by weight, more preferably between 15 and 60% by weight, in order that benzene in the material could be efficiently converted into other aromatic hydrocarbons.

More preferably, the starting material for the invention contains C9+ alkyl-aromatic hydrocarbons, even more preferably C9 and C10 alkyl-aromatic hydrocarbons. C9 alkyl-aromatic hydrocarbons include trimethylbenzene, ethyltoluene and propylbenzene; and C10 alkyl-aromatic hydrocarbons include tetramethylbenzene, ethylxylene, diethylxylene, propyltoluene and butylbenzene. Of those, preferred are trimethylbenzene and tetramethylbenzene. The C9+ alkyl-aromatic hydrocarbon content of the starting material is not specifically defined, but preferably falls between 5 and 90% by weight for efficient transalkylation of the alkyl-aromatic hydrocarbons with benzene. More preferably, it falls between 7 and 85% by weight, even more preferably between 10 and 80% by weight.

More concretely, in the invention, the aromatic hydrocarbon material containing benzene and C9+ aromatic hydrocarbons and having a non-aromatic compound content of at most 1% by weight is preferably transalkylated to give the intended product. As the case may be, the product may be further transalkylated. The transalkylation includes, for example, formation of toluene and xylene from benzene and trimethylbenzene; formation of toluene, xylene and trimethylbenzene from benzene and tetramethylbenzene; formation of toluene from benzene and xylene; formation of xylene from toluene and trimethylbenzene; formation of xylene and trimethylbenzene from toluene and tetramethylbenzene; and formation of ethylbenzene from benzene and diethylbenzene. Without being limited to these, it may include any other different types of transalkylation. Through the conversion, benzene and C9+ aromatic hydrocarbons in the starting material all decrease, while C7 and C8 aromatic hydrocarbons in the product increase. C7 and/or C8 aromatic hydrocarbons extracted out of the product may be used for producing industrial compounds. The remaining part of the product could be recycled.

In the invention, the transalkylation may be accompanied by disproportionation, dealkylation or alkylation.

The catalyst to be used in the invention is for converting aromatic compounds. Concretely, it may be any one for transalkylation. As the case may be, the catalyst may induce disproportionation, dealkylation or alkylation. Preferably, the catalyst has the capability of selectively dealkylating and transalkylating ethyl and propyl groups, but having no influence on methyl groups. Concretely, preferred are morphology-selective metallosilicate catalysts, and more preferred are crystalline aluminosilicates. Especially preferred is zeolite, which may be any of mordenite, or Y, X, beta or ZSM-5 zeolite, but is more preferably mordenite.

Zeolite for use in the invention may be ion-exchanged with suitable metal ions, or hydrogen ions. Preferred are hydrogen-exchanged zeolite.

For the catalyst, optionally used is a binder. The binder is not specifically defined, including, for example, inorganic oxides such as alumina, silica-alumina, titania, magnesia, etc.; clays such as montmorillonite, kaolin, sepiolite, acid clay, etc. Either singly or as combined, any of these may be used herein as the binder. Of these, preferred is alumina. The amount of the binder for use herein is not also specifically defined, but preferably falls between 20 and 60% by weight of the catalyst.

Preferably, the catalyst has a hydrogenation-active site therein to ensure improved activity and prolonged life. Any one having hydrogenation activity is employable herein for the catalyst. Zeolite for the catalyst may have hydrogenation activity by itself, but is preferably combined with at least one metal selected from metals of Groups VIB, VIIB and VIII of the Periodic Table. Concretely, the Group VIB metal includes chromium, molybdenum and tungsten; the Group VIIB metal includes manganese, technetium and rhenium; the Group VIII metal includes iron, ruthenium, osmium, cobalt, rhodium, iridium, nickel, palladium and platinum, but preferably nickel, palladium and platinum. More preferred is rhenium. Preferably, the catalyst carries any of the metals or their compounds. The metal may be introduced into catalyst by, for example, ion exchange, impregnation, adsorption from the gaseous phase, introduction during zeolite synthesis adsorption of metal vapor, and any known method. The amount of the metal to be introduced into the catalyst is not specifically defined, and may be suitably determined depending on the reaction condition, etc. Preferably, it may fall between 0.001 and 10% by weight, more preferably between 0.01 and 5% by weight, even more preferably between 0.02 and 2% by weight of the catalyst.

EXAMPLES

The invention is described more concretely with reference to the following Examples.

Example 1

105 g of powdery, sodium-type synthetic mordenite, 45 g of α-alumina, 12 g of alumina sol (having an alumina content of 10% by weigh), 10.5 g of alumina gel (having an alumina content of 70% by weight), and a suitable amount of ion-exchanged water were mixed and kneaded for about 2 hours, then shaped into noodles having a size of 1.2 mmφ (outer diameter)×1.0 mm (length), and dried at 120° C. for 16 hours. 50 g of the noodles (dried at 120° C.) were calcined at 400° C. in air for 5 hours, and then processed with 100 g of an aqueous 10 wt. % ammonium chloride solution at 80 to 85° C. for 1 hour. After having been separated from the liquid through filtration, these were washed with water.

These were further processed with 100 g of an aqueous 5 wt. % tartaric acid solution at 80 to 85° C. for 3 hours, separated from the liquid through filtration, and washed with water. Then, these were dipped in 6.5 g of an aqueous 5 wt. % rhenium(VII) oxide solution at room temperature. After having been dried at 120° C. for 16 hours, these were calcined in air at 540° C. for 8 hours. Thus was prepared an H-type synthetic mordenite catalyst. The catalyst was loaded into a fixed-bed reactor, and a starting material, from which the non-aromatic compounds had been removed through distillation, was contacted with the catalyst in the reactor. Before and after removal of the non-aromatic compounds, the composition of the starting material is given in Table 1; and the composition of the product obtained herein is also given therein. The reaction condition is as follows:

Reaction Condition:

| | |
|---|---|
| Temperature | 400° C. |
| Pressure | 2.5 Mpa-G |
| Liquid hourly space velocity | 2.3 hrs$^{-1}$ |
| Hydrogen/starting material | 4.0 mol/mol |

The hydrogen consumption throughout the reaction was 0.84% by weight relative to the starting material; and the catalyst deactivation rate was −0.04 wt. %/100 hrs, calculated from the xylene content of the product.

TABLE 1

| Constituent Ingredients | Composition of Crude Material before removal of non-aromatic compounds (wt. %) | Composition of Starting Material after removal of non-aromatic compounds (wt. %) | Composition of Product after 100 hours (wt. %) |
|---|---|---|---|
| Non-aromatic Compounds | 10.0 | 0.1 | 10.7 |
| Benzene | 21.3 | 22.6 | 8.0 |
| Toluene | 1.3 | 1.4 | 27.7 |
| C8 Aromatic Compounds | 0.3 | 0.3 | 33.5 |
| C9 Aromatic Compounds | 62.3 | 70.2 | 17.6 |
| C10 Aromatic Compounds | 4.8 | 5.4 | 2.5 |

Comparative Example 1

The crude material used in Example 1 was, without being subjected to distillation, directly contacted with the catalyst under the same condition as in Example 1. The data obtained are given in Table 2. In this, the hydrogen consumption throughout the reaction was 1.14% by weight; and the catalyst deactivation rate was −0.08 wt. %/100 hrs.

TABLE 2

| Constituent Ingredients | Composition of Starting Material (wt. %) | Composition of Product after 100 hours (wt. %) |
|---|---|---|
| Non-aromatic Compounds | 10.0 | 19.5 |
| Benzene | 21.3 | 7.7 |
| Toluene | 1.3 | 25.8 |
| C8 Aromatic Compounds | 0.3 | 29.7 |
| C9 Aromatic Compounds | 62.3 | 15.1 |
| C10 Aromatic Compounds | 4.8 | 2.2 |

From the data in Tables 1 and 2, it is understood that, in the process of contacting the benzene-containing aromatic hydrocarbon material, of which the non-aromatic hydrocarbon content is not larger than 1% by weight, with the catalyst, the aromatic compounds in the material are efficiently converted into useful aromatic hydrocarbons such as toluene and xylene.

While the invention has been described in detail and with reference to specific embodiments thereof, it will be apparent to one skilled in the art that various changes and modifications can be made therein without departing from the spirit and scope thereof.

What is claimed is:

1. A method for converting a crude starting material comprising 5 to 80% by weight of benzene, other aromatic hydrocarbons and non-aromatic compounds in an amount of at least about 10% by weight to useful C7 and C8 aromatic hydrocarbons comprising:
   (A) lowering the content of said non-aromatic compounds by distillation to produce a material having a non-aromatic compound content of about 0.1% by weight or less, and
   (B) reacting said material having a non-aromatic compound content of about 0.1% by weight or less in the presence of hydrogen and a catalyst containing H-type synthetic mordenite and between about 0.02 to 2% by weight rhenium at a pressure of from 0.1 to 100 MPa and a temperature of from 200 to 650° C. to diminish the benzene content of said material having a non-aromatic compound content of about 0.1% by weight or less and convert at least a portion of said material having a non-aromatic compound content of about 0.1% by weight or less into C7 or C8 aromatic hydrocarbons wherein said aromatic hydrocarbon conversion reaction is transalkylation reducing benzene content and C9 content to increase the contents of xylene and toluene in the product.

2. The method for converting aromatic hydrocarbons as claimed in claim 1, wherein the material having a non-aromatic compound content of about 0.1% by weight or less contains C9+ alkyl-aromatic hydrocarbons.

3. The method for converting aromatic hydrocarbons as claimed in claim 1, wherein said benzene and said C9+ aromatic hydrocarbons in the material having a non-aromatic compound content of about 0.1% by weight or less are reduced and C7 and C8 aromatic hydrocarbons in the product are produced.

4. The method defined in claim 1, wherein hydrogen is present in contact with said material having a non-aromatic compound content of about 0.1% by weight or less and said catalyst, and wherein said hydrogen has a flow rate of 0.1 and 20 mol/mol in terms of hydrogen/material having a non-aromatic compound content of about 0.1% by weight or less.

5. The method of claim 1, wherein the reaction pressure is between 0.5 and 60 MPa and the reaction temperature is between 250 and 500° C.

* * * * *